(12) United States Patent
Galbraith et al.

(10) Patent No.: US 9,320,853 B2
(45) Date of Patent: *Apr. 26, 2016

(54) METHOD FOR ADMINISTERING A FLUID ACTIVE SUBSTANCE FROM A MULTI-CHAMBER AMPOULE

(71) Applicant: TECPHARMA LICENSING AG, Burgdorf (CH)

(72) Inventors: Sofia Galbraith, Solothurn (CH); Ulrich Moser, Heimiswil (CH); Juerg Hirschel, Aarau (CH); Ian Thompson, Burgdorf (CH)

(73) Assignee: TecPharma Licensing AG, Burgdorf (CH)

(*) Notice: Subject to any disclaimer, the term of this patent is extended or adjusted under 35 U.S.C. 154(b) by 368 days.

This patent is subject to a terminal disclaimer.

(21) Appl. No.: 13/862,871

(22) Filed: Apr. 15, 2013

(65) Prior Publication Data

US 2013/0310739 A1 Nov. 21, 2013

Related U.S. Application Data (63) Continuation of application No. 12/572,796, filed on Oct. 2, 2009, now Pat. No. 8,439,864, which is a continuation of application No. PCT/EP2008/002341, filed on Mar. 25, 2008.

(30) Foreign Application Priority Data

Apr. 5, 2007 (DE) .......................... 10 2007 016 811

(51) Int. Cl.
*A61M 5/20* (2006.01)
*A61M 5/24* (2006.01)
(Continued)

(52) U.S. Cl.
CPC ............... *A61M 5/24* (2013.01); *A61M 5/2448* (2013.01); *A61M 5/31551* (2013.01);
(Continued)

(58) Field of Classification Search
CPC . A61M 5/24; A61M 5/2448; A61M 5/31551; A61M 2005/3125; A61M 2205/583
See application file for complete search history.

(56) References Cited

U.S. PATENT DOCUMENTS

| | | | |
|---|---|---|---|
| 4,449,645 A | 5/1984 | Korwin et al. | |
| 4,968,299 A * | 11/1990 | Ahlstrand et al. | 604/90 |
| 5,993,412 A | 11/1999 | Deily et al. | |
| 6,406,455 B1 * | 6/2002 | Willis et al. | 604/68 |
| 6,645,179 B1 | 11/2003 | Ishikawa et al. | |
| 6,793,646 B1 | 9/2004 | Giambattista et al. | |
| 6,960,184 B2 | 11/2005 | Willis et al. | |

FOREIGN PATENT DOCUMENTS

| | | |
|---|---|---|
| DE | 10 2004 055 298 A1 | 5/1996 |
| DE | 100 36 594 A1 | 2/2002 |

(Continued)

*Primary Examiner* — Bhisma Mehta
*Assistant Examiner* — Bradley Osinski
(74) *Attorney, Agent, or Firm* — Dorsey & Whitney LLP; Stuart R. Hemphill, Esq.

(57) ABSTRACT

An administering device for administering an active substance from a multi-chamber container comprising a first chamber holding a solid active substance and a second chamber holding a dissolving liquid for the active substance, wherein the administering device comprises a mixing device for mixing the active substance with the dissolving liquid and a housing accommodating the mixing device, the container being moveable relative to the housing, and the administering device further comprising a first indicator for indicating a position of the container relative to the housing upon completion of a mixing step, and a second indicator for indicating a position of the container relative to the housing upon completion of a venting step.

10 Claims, 7 Drawing Sheets

(51) Int. Cl.
  *A61M 5/31*    (2006.01)
  *A61M 5/315*   (2006.01)
  *A61M 5/50*    (2006.01)

(52) U.S. Cl.
  CPC ......... *A61M 5/3146* (2013.01); *A61M 5/31505* (2013.01); *A61M 5/31535* (2013.01); *A61M 5/31591* (2013.01); *A61M 5/50* (2013.01); *A61M 2005/3125* (2013.01); *A61M 2005/31508* (2013.01); *A61M 2205/583* (2013.01)

(56) References Cited

FOREIGN PATENT DOCUMENTS

| EP | 0 298 067 B1 | 10/1991 |
| EP | 1 392 377 A | 3/2004 |
| WO | WO 01/30425 A | 5/2001 |
| WO | WO 2004/028598 A | 4/2004 |
| WO | WO 2006/057604 A | 6/2006 |

\* cited by examiner

METHOD FOR ADMINISTERING A FLUID ACTIVE SUBSTANCE FROM A MULTI-CHAMBER AMPOULE

CROSS-REFERENCED RELATED APPLICATIONS

This application is a continuation of U.S. Ser. No. 12/572,796 filed Oct. 2, 2009, which is a continuation of International Patent Application No. PCT/EP2008/002341 filed Mar. 25, 2008, which claims priority to German Patent Application No. DE 10 2007 016 811.1 filed Apr. 5, 2007, the entire contents of each are incorporated herein by reference.

BACKGROUND

The present invention relates to devices for injecting, administering, infusing, dispensing or delivering a substance, and to methods of making and using such devices. More particularly, it relates to an administering device for administering a liquid agent, e.g., a medicinal or therapeutic substance or product, from a multi-chamber carpule or ampoule, e.g. a two-chamber carpule, multi-chamber container or reservoir, multi-chamber ampoule, etc.

Various agents, such as growth hormone for example, can not be stored for any length of time dissolved in a liquid. However, to provide successful treatment for growth hormone problems, for example, it is necessary to introduce such agents into a patient's body tissue in liquid form. Administering devices, e.g., injection pens, may be used for this purpose. To enable such substances with a short shelf-life to be made available in a liquid medium for administering with injection devices, multi-chamber carpules, e.g. two-chamber carpules or ampoules, have been developed, in which an agent in a dried or lyophilized form is stored in a first carpule chamber and a dissolving liquid is stored in a second carpule chamber separately from the agent. The two chambers are usually separated from one another by displaceable stoppers. The first chamber usually comprises an outlet of the carpule closed by a membrane, for example, the carpule wall and a first stopper. The second chamber usually adjoins the first chamber and is formed by the first stopper, the carpule wall and a second stopper. Along the longitudinal axis of the carpule and hence along the axis along which the stopper can be pushed, a bypass is provided in the carpule wall, which can be used as a bypass for the dissolving liquid around the first stopper. To mix the agent with the dissolving liquid, a pressure is applied to the second stopper inside the carpule, which is transmitted to the first stopper by the non-compressible dissolving liquid. The two stoppers are therefore moved along the longitudinal axis of the carpule relative to the carpule wall. As soon as the first stopper has moved so that it lies in the region of the carpule bypass, the dissolving liquid passes out from the second chamber through the bypass and into the first chamber containing the agent. The second carpule stopper can be pushed relative to the carpule wall and toward the first stopper until it lies against the first stopper. When the second stopper is pushed again, the first stopper is moved with it and the dissolving liquid together with the agent can be dispensed through the carpule opening. To this end, an injection needle is fitted on the carpule opening, which is able to establish a fluid connection to the first carpule chamber. When mixing the agent with the dissolving liquid, care must be taken to ensure that the agent is not exposed to excessive flows of dissolving liquid. Foaming should be avoided during mixing as far as possible. The agent is then ready in dissolved form and can be injected into the patient's tissue with conventional administering devices.

Patent specification DE 10 2004 055 298 A1 discloses a mixing device for a two-chamber carpule (or ampoule), in which a two-chamber carpule is accommodated in a mixing sleeve, and the mixing sleeve is fitted by an axial movement toward an administering device. According to the English abstract (available from the esp@cenet database), it further relates to a device for mixing injected medicine comprising an ampoule sleeve for receiving an ampoule with medicine, a mixing sleeve with a mixing path, an abutment and a guiding unit having a power transmission structure which converts a linear movement in the axial direction of the mixing device into a rotary movement. As the mixing sleeve is pushed on, the stoppers of the two-chamber carpule are moved inside the carpule and the agent is mixed with the dissolving liquid.

Patent specification EP 0 298 067 B1 (the English equivalent is U.S. Pat. No. 4,968,299) discloses an arrangement in which the carpule is inserted in a carpule sleeve and the carpule sleeve is screwed into the housing of an administering device. Due to the axial movement during the screwing-on operation, the stoppers are moved inside the two-chamber carpule and the agent is mixed with the dissolving liquid. The devices known from the prior art enable the agent to be mixed slowly to avoid foaming or prevent damage to the agent.

For users of these types of devices, however, it is difficult to tell when the mixing procedure is complete and the agent has therefore been fully dissolved in the dissolving liquid in the desired concentration. Before administering an agent in liquid form into a patient's tissue by an administering device, it is necessary to vent the liquid duct between the carpule chamber in which the liquid is contained and the tip of an injection needle. This operation may be thought of and/or referred to as priming. In the case of the administering operation which takes place using two-chamber carpules known from the prior art, the priming operation must be actively carried out by the user and may be, therefore, forgotten before administering a liquid agent.

SUMMARY

An object of the present invention is to provide a device for administering an agent from a multi-chamber carpule (or ampoule or other suitable container), which simplifies the sequence of use of the device and helps ensure that a dose of the agent is simply and reliably set and administered.

In one embodiment, the present invention comprises an administering device for administering an active substance from a multi-chamber container comprising a first chamber holding a solid active substance and a second chamber holding a dissolving liquid for the active substance, wherein the administering device comprises a mixing device for mixing the active substance with the dissolving liquid and a housing accommodating the mixing device, the container being moveable relative to the housing, and the administering device further comprising a first indicator for indicating a position of the container relative to the housing upon completion of a mixing step, and a second indicator for indicating a position of the container relative to the housing upon completion of a venting step.

In one embodiment, the present invention comprises a device for administering an active substance from a multi-chamber carpule comprising at least one first chamber holding a solid active substance and a second chamber holding a dissolving liquid for the active substance, wherein the administering device further comprises a mixing device for mixing the active substance with the dissolving liquid and a housing accommodating the mixing device, wherein the carpule is moveable relative to the housing, and the administering device further comprises at least one first indication for marking or indicating a position of the multi-chamber carpule relative to the housing upon completion of the mixing step and a second indication for marking or indicating a position of the carpule relative to the housing upon completion of a venting step of the carpule.

In one embodiment, an administering device in accordance with the present invention, e.g. an administering device for use with multi-chamber carpules, has a display system comprising at least a first display for indicating a position of the carpule relative to a housing of the device on completion of a mixing operation and a second display for indicating a position of the carpule relative to the housing of the device on completion of a priming operation. The displays may also operate on the basis of a catch position. It should be appreciated that the multi-chamber carpule may be a two-chamber carpule, that it would also be possible to provide more than two chambers inside such a carpule, for example to provide two different agents in solid form or alternatively two different dissolving liquids, and that any carpule may also be thought of and/or referred to as a container or ampoule.

In some embodiments, to mix the agent inside a carpule, an administering device in accordance with the present invention may have a drive member, for example in the form of a plunger rod, which is used to push the stoppers inside the carpule relative to the carpule wall as the multi-chamber carpule is being inserted and to dispense the agent and liquid from the carpule following mixing. The mixing operation may be effected by pushing on or screwing on a holder element or carpule holder for the multi-chamber carpule onto or into a housing of the administering device. A simple thread may be provided between the housing and carpule holder for this purpose, for example. However, it would also be possible to provide a mixing device with a mechanism with a gear ratio or a mechanism, e.g. as disclosed in DE 10 2004 055 298 A1. Other mixing devices known from the prior art may also be used within the context of the present invention.

In some preferred embodiments, catch positions used to indicate the individual positions during the individual steps involved in preparing the administering device, such as mixing, priming and setting the dose, are provided in the form of an anti-backslide lock or anti-rotation lock, in which case it is no longer possible to remove the holder element from the housing in the direction opposite to that in which it was inserted. It would also be possible for the anti-backslide lock or anti-rotation lock to be of a releasable design, so that the lock can be released if desired.

In some embodiments, in the initial state or initial position of the holder element with respect to the housing, prior to mixing, the multi-chamber carpule or carpule holder assumes a first position relative to the housing or plunger rod of the administering device. The carpule is moved out of this initial position in the direction into the housing until it reaches a position relative to the housing in which mixing of the agent with the dissolving liquid is complete. In some embodiments, the display system in accordance with the present invention has a first display which indicates this position, i.e. the mixing position, in which the dissolving liquid has passed completely out of the second carpule chamber into the first carpule chamber containing the solid agent. Following a further movement of the carpule in the housing in the proximal (rearward) direction or in the direction toward the plunger rod of the administering device, a priming operation takes place, which is intended to remove any air left in the first chamber from the carpule. To this end, the stoppers of the carpule are pushed jointly. In some embodiments, this second position of the carpule relative to the housing, namely the priming position in which the priming operation has terminated, is indicated by a second display of the display system.

Using an administering device in accordance with the present invention, a user can easily take a reading from the administering device or is able to tell by acoustic perception whether a mixing operation and a subsequent priming operation have been fully and correctly performed. He or she can therefore be sure that the administering device is ready and that a correct dose will be dispensed when administered.

In one embodiment of the present invention, the display system has a third display, which indicates the initial position of a carpule relative to the housing or relative to the plunger rod, i.e. the position of the stoppers inside the carpule, prior to starting a mixing operation. Since the mixing operation takes place across a longer distance of the carpule relative to the housing or to the stopper inside the carpule, it is also possible to provide the third display in the form of several display elements, which indicate the progress of the mixing operation. A series of numbers or characters may be provided for this purpose, for example, or alternatively a bar which becomes narrower or wider during the course of mixing, or it may be that a clicking noise can be repeatedly heard. The visual displays of the display system may be axially offset along a longitudinal axis of the administering device. However, the displays may also be disposed around the circumference of the administering device. The displays may also be based on a combination of these options, i.e. the individual displays are disposed both axially and offset in the circumferential direction.

In one embodiment, an administering device in accordance with the present invention has a housing and a holder element in the form of a carpule holder as described above, and the carpule holder can be moved relative to the housing of the administering device to mix the agent and dissolving liquid. A pointer or a cut-out may be provided on the carpule holder or on the housing, which can be selected or identified by a visual display during the movement of the carpule holder relative to the housing. The visual displays for the display system are provided on the other respective parts, namely the carpule holder and housing. When the carpule holder is moved relative to the housing, the pointer on the carpule holder may firstly point to the indicator of the initial position, for example, and then to the indicator of the mixing position and finally to the indicator of the end position of priming, namely the venting position. It would also be possible for the displays to appear inside a cut-out or an orifice of the carpule holder in the respective position. Finally, it is also possible to opt for a combination of the individual displays on the carpule holder and housing. For example, the display for the initial position may be provided on the carpule holder and the display for the mixing position and for the priming or venting position may be provided on the housing. Pointers are provided accordingly on the carpule holder and housing, which identify the displays.

In an exemplary embodiment, the displays are provided in the form of visually perceptible markings. As mentioned above, the visual display elements used might be characters, numbers, color coding, different shapes such as triangles, squares, circles and dots or other suitable indicia. Naturally, a combination of these display elements would also be possible.

As described above, a display system of an administering device in accordance with the present invention may also be disposed on the carpule itself. In this case, the displays may be provided in the form of markings along the carpule and the pointers for selecting the markings may be disposed on the stopper of the carpule for example, e.g. the second stopper of the carpule. A front or rear edge of the stopper may also be used as the pointer. If a two-chamber carpule is inserted in a carpule sleeve, an elongate slot may be provided in the carpule sleeve for example, through which a reading can be taken from the display system on the carpule.

In some embodiments of a method for preparing an administering device with a multi-chamber carpule in accordance with the present invention, the end of the mixing operation is indicated by a first display and the end of a priming operation is indicated by a second display.

In some preferred embodiments of the device and method, a third display indicates the initial position of the multi-chamber carpule relative to a housing of the administering device. During mixing in a two-chamber carpule, i.e. as the stopper is pushed inside the carpule, the first display appears first of all at the end of the mixing operation. As the stopper is moved farther inside the carpule, the second display appears, indicating the end of priming.

In principle, it would also be possible to use displays in the form of acoustically perceptible signals. For example, the display for the mixing end position may be a clicking signal and the display for the venting end position may be a knocking signal different from the clicking signal. However, it would also be possible to indicate all the positions using the same noise. The noise of the clicking or knocking may be produced by suitable mechanical catch or stop mechanisms inside the administering device for example, which are operated during mixing in the two-chamber carpule.

In another embodiment of the present invention, a device for administering a liquid product is provided with a catch or display mechanism for inserting the holder element in the housing. To prevent misuse of the device, this firstly ensues that, having started to introduce the holder element into the housing, each and every preparation step which has been completed can not be reversed. Secondly, the end of the individual preparation steps is indicated by a display. In this respect, the indication may be provided in the form of the acoustically perceptible latching sound. A lock or locking means are provided for this purpose for example, by which the holder element is blocked or locked in place after every preparation step to prevent a movement in the direction opposite that in which it was introduced into the housing. It is also optionally possible to use a lock of a releasable design, if practical.

In some embodiments, e.g. in the case of a thread guide between the housing and holder element, the lock may be provided in the form of an anti-rotation lock to prevent the holder element from being screwed back out of the housing. Such an anti-rotation lock might be provided in the form of a resilient or snap arm on the holder element or on the housing, which latches in a recess in the housing or holder element in the reverse direction of rotation but is able to slide out of the recess in the forward direction. Such an anti-rotation lock is activated when the mixing operation and venting operation have terminated for example. In addition, such an anti-rotation lock may be already activated when the holder element is inserted in the housing. In other words, the holder element is already secured by a lock in the initial position to prevent it from being completely screwed back out of the housing. The catch system simultaneously serves as the indication that the corresponding preparation step has been completed. In the inserted position after mixing and venting, the lock may be designed so that a movement in the proximal direction, i.e. a screwing-in movement, is also prevented. This being the case, the holder element is secured in the inserted position after priming so that it can not be inserted or pulled out or screwed in or out.

In some embodiments, the locks or anti-rotation locks are designed so that on latching or snapping into the lock, an acoustic signal in emitted at the same time so that the end of the individual preparation steps is audible. The sequence of the individual preparation steps will therefore be acoustically indicated to the user.

In accordance with the present invention, the anti-backslide or anti-rotation lock system used for the holder element is an improvement in injection devices, without incorporating a display or indicator in accordance with the present invention. Thus, some embodiments of the present invention are directed to a lock system, some to an indicator or display, and some to both.

BRIEF DESCRIPTION OF THE DRAWINGS

The drawings illustrate two exemplary embodiments of an administering device in accordance with the present invention. Features which become apparent from the drawings should be interpreted as falling within the scope of the present invention, although the drawings should not be construed as restricting the present invention in any way.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless stated otherwise, positional terms (e.g., up, down, front, rear, distal, proximal, etc.) are descriptive not limiting. Same reference numbers are used to denote same parts or components.

Figure 1A:
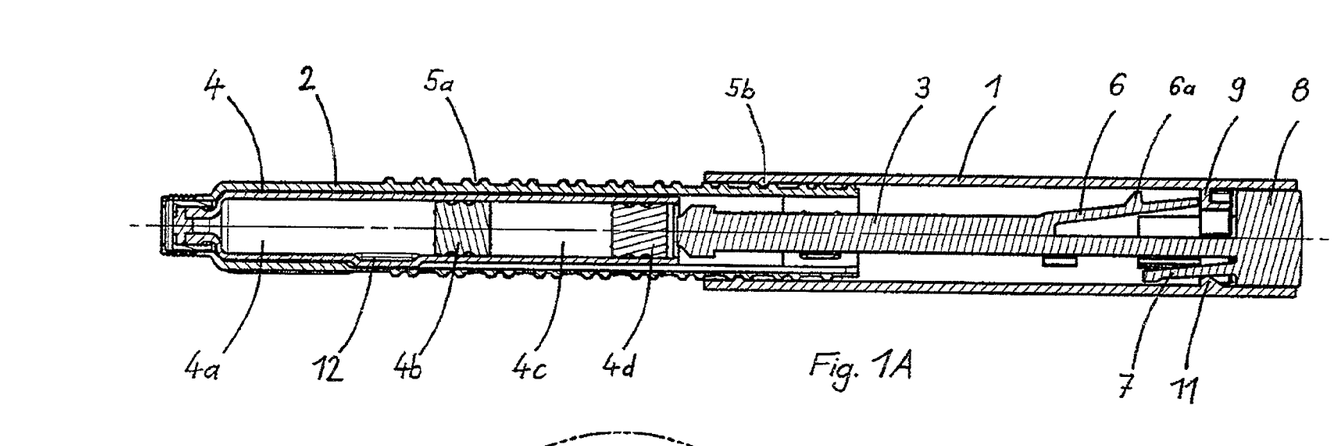
FIG. 1A illustrates an embodiment of an administering device in accordance with the present invention, disposed in an initial position.

FIG. 1A illustrates one embodiment of a device for administering a liquid product in accordance with the present invention, disposed in an initial position. The device has a housing 1, a holder element 2 and a drive element 3. In some embodiments, a device in accordance with the present invention comprises and is able to operate with these three components alone. In other embodiments, a product reservoir containing a desired product to be administered and a correctly fitting injection needle may be added.

In the case of the embodiment illustrated as an example, the product reservoir is a two-chamber reservoir or two-chamber carpule, comprising a first chamber 4a bounded by a stopper 4b and a second chamber 4c bounded by the first stopper 4b and another, second stopper 4d. Also provided in the circumference of the wall of the product reservoir is a bypass 12 (see FIGS. 4a and 5a), through which a suitable dissolving solvent or agent can be transferred from the second chamber 4c into the product chamber 4a, in a manner known in the art.

At its proximal (rear) end, the holder element 2 is partially inserted in the distal (front) end of the housing 1. A guide structure is provided between the housing 1 and holder element 2, which effects a relative movement between the housing 1 and holder element 2. The guide structure comprises a thread-type guide groove 5a extending around the external circumferential surface of the sleeve-shaped holder element 2. Disposed on the internal circumferential surface of the housing 1, which is likewise sleeve-shaped, is a complementary guide cam 5b, which is guided inside the guide groove 5a. The guide cam 5b may also be provided in the form of a guide track or guide segment. The guide structure in the embodiment illustrated as an example here is a thread guide. The holder element 2 is inserted axially into the housing in the proximal direction by a rotating movement of the holder element 2 relative to the housing 1.

The drive element 3 comprises a rod-shaped design. In the initial state illustrated in FIG. 1A, the distal end of the drive element 3 moves so that it lies opposite the proximal stopper 4d of the product reservoir 4.

In the initial position illustrated in FIG. 1A, the administering device is in the state corresponding to that in which it is sold, the device being sold, or provided or issued to the user in this state.

At its proximal end, the drive element 3 has a retaining element 6 and an activator element 7. In some embodiments, the retaining element 6 and the activator element 7 are an integral part of the drive element 3. However, it would also be possible for the retaining element 6 and activator element 7 to be joined to the rod-shaped region of the drive element. At the proximal end, the drive element 3 also has a thicker region, which may be termed a drive knob 8. The drive knob 8 can not be accessed by the user in the initial position because it is recessed in the housing 1.

The retaining element 6 and activator element 7 project laterally out from the drive element in the form of flexible projections or arms. In principle, it would also be possible to provide two or more such arms on the drive element. The retaining element 6 projects out from the drive element 3 in the proximal direction and the activator element in the distal direction.

In the initial position illustrated in FIG. 1A, the retaining element 6 is opposite an inwardly projecting projection or an edge 9 of the housing in the axial direction. Accordingly, the proximal end of the retaining element sits in abutment with the housing projection 9 in the axial direction. In this position, the retaining element is in its base position. However, the retaining element can be flexibly biased so that it can be moved in the radial direction toward the axis of the drive element 3. The activator element 7 extends down from the drive element 3 at an angle in the distal direction. The activator element is in a relaxed state in the initial position but can be flexibly deflected outwardly in the radial direction toward the drive element axis. During preparation of the administering device, they provide different functions for controlling the sequence of individual preparation steps. In conjunction with the drive element, they may be thought of and/or referred to as the control mechanism for the sequence control.

Figure 1B:
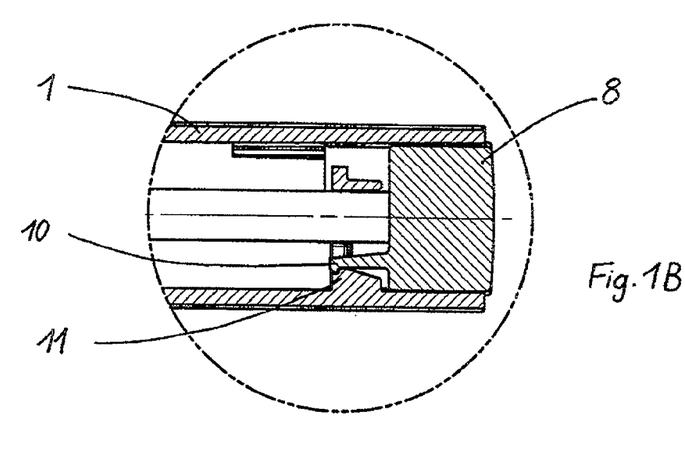
FIG. 1B is a detailed view of the administering device illustrated in FIG. 1A, in a view rotated by 90°.

FIG. 1B shows a detailed view of the proximal region of the administering device illustrated in FIG. 1A, in which the device has been rotated by 90°. A lock element 10 may be seen, which co-operates with a projection 11 on the housing 1. Together, the lock element 10 and projection 11 constitute a clamp connection to secure the lock element 3 in addition to the locking action provided by the contact between the retaining element 6 and housing projection 9 and the contact between the drive button 8 and housing projection 9.

The contact between the retaining element 6 and the housing projection 9 in the axial direction affords a blocking action against a movement of the drive element in the proximal direction relative to the housing. The contact between the drive knob 8 and housing projection 9, on the other hand, blocks the drive element 3 relative to the housing in the distal direction.

Figure 2:
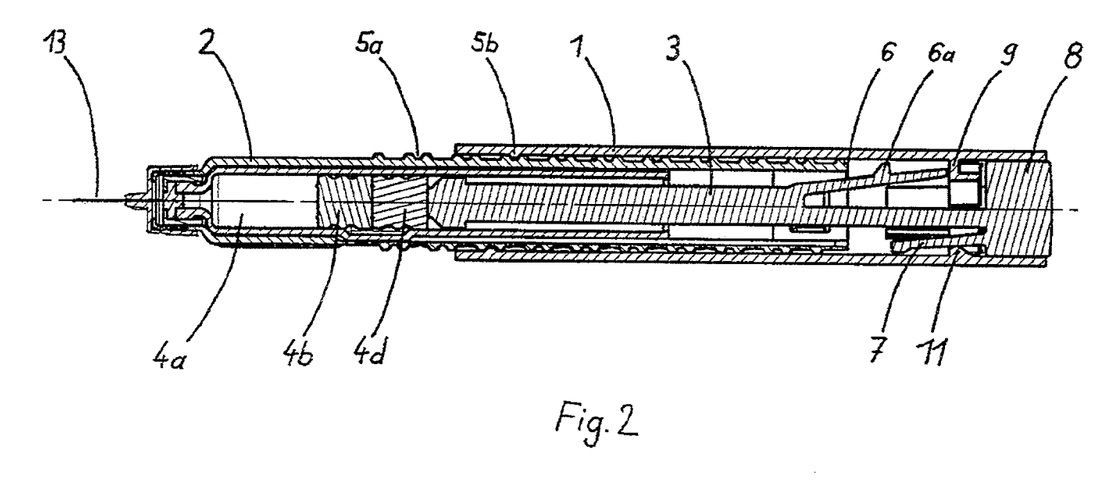
FIG. 2 illustrates the administering device of FIG. 1A in a mixing position.

FIG. 2 shows the administering device in a mixing position. An injection needle 13 has been fitted on the end of the device. From the initial position illustrated in FIG. 1A, the holder element 2 is introduced into the interior of the housing relative to the housing 1 in the proximal direction and/or screwed in along the guide structure. During this operation, the drive element 3 remains fixed relative to the housing by the blocking action between the retaining element 6 and housing projection 9 and also by the locking action between the lock element 10 and the projection 11 relative to the housing. Introducing the holder element 3 moves the distal end of the drive element 3 into contact with the stopper 4d of the product reservoir 4 and pushes it in the distal direction as the introduction movement inside the product reservoir continues. As a result, the driving force is transmitted firstly by the dissolving in the chamber 4c to the stopper 4b so that both stoppers 4b and 4d are driven distally. As soon as the stopper 4b has moved so that it lies in the region of the bypass, the stopper 4b remains stationary relative to the reservoir. The stopper 4d, on the other hand, is driven further so that the dissolving material passes out of chamber 4c through the bypass into chamber 4a, where it can dissolve an agent disposed there. The stopper 4d is driven until it hits the stopper 4b. As a result, the mixing position of the administering device is reached. During this operation, the holder element 2 continues to be introduced farther into the housing 1. However, the drive element 3 remains stationary.

Figure 3:
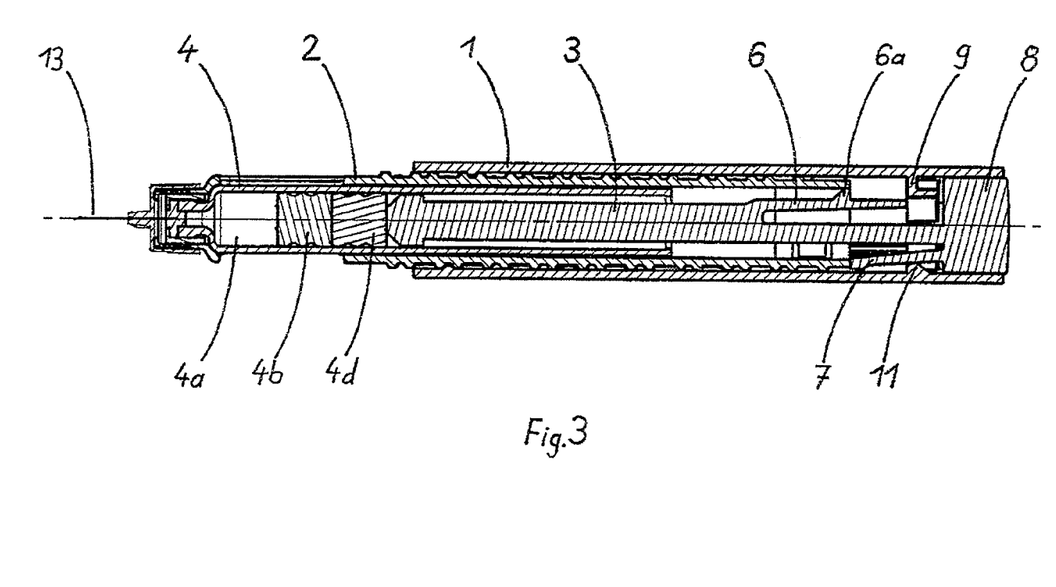
FIG. 3 illustrates the administering device of FIG. 1A in a priming position.

FIG. 3 illustrates the administering device in a priming position. From the mixing position illustrated in FIG. 2, the holder element 2 is inserted further into the housing 1 in the proximal direction. So far, the holder element 2 has been inserted into the housing across a first insertion distance, during which the holder element 2 remained in the retaining position. The proximal edge of the holder element 2 now abuts with a shoulder 6a on the retaining element 6. The shoulder 6a has an oblique plane which is aligned relative to the proximal end of the holder element. When the holder element 2 is pushed farther into the housing across a second insertion distance, the proximal end hits the oblique surface of the shoulder 6a and slides down this surface. As this happens, the retaining element 6 is deflected outward in the radial direction toward the axis of the drive element 3. The retaining element 6 in the form of an operating arm is deflected out of contact with the housing projection 9. From the mixing position to this triggered position, in which the retaining element 6 of the drive element 3 is deflected out of its retaining position for retaining the drive element 3 relative to the housing 1, the holder element 2 covers a second insertion distance, which can be termed a release distance. As soon as the retaining element 6 has been deflected out of contact with the housing projection 9, the proximal end of the holder element 2 moves against the distal end of the activator element 7. The drive element 3 can now be moved relative to the housing 1 in the proximal direction across a third insertion distance. During a further forward movement of the holder element 2 relative to the housing 1 to deflect the retaining element 6, the stoppers 4b and 4d are also simultaneously pushed farther in the distal direction of the product reservoir 4. Any superfluous air is therefore able to escape from the product chamber 4a via the injection needle 13. In principle, it would also be conceivable to terminate the priming operation on covering the first insertion distance, in which case only the release of the retaining position of the retaining element would take place during the second and third insertion distance.

Figure 4A:
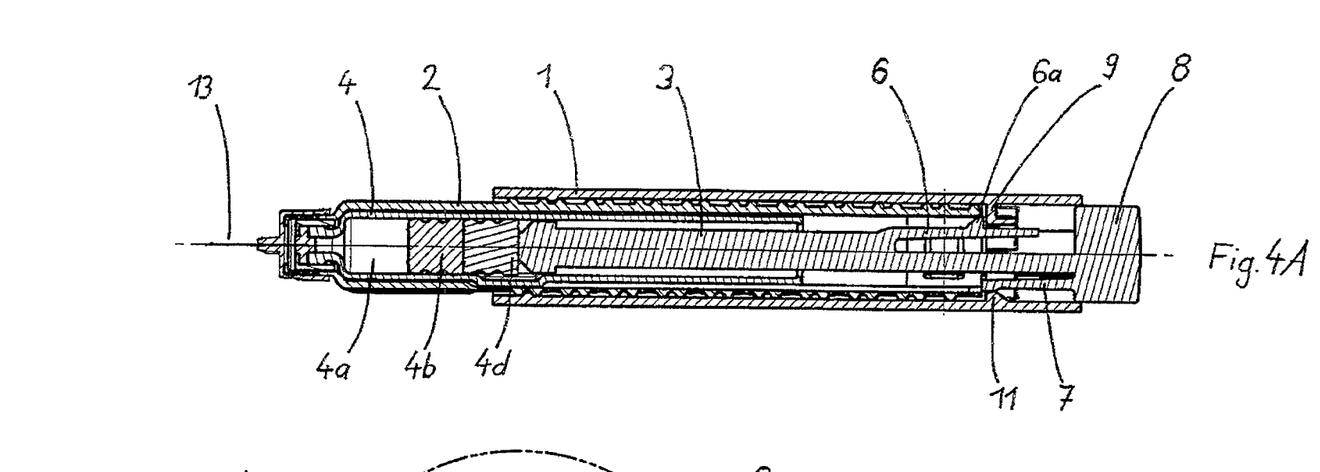
FIG. 4A illustrates the administering device of FIG. 1A in an inserted position.

FIG. 4A illustrates the administering device in an inserted position, in which the holder element is inserted in the housing in the proximal direction, having completely travelled across the third insertion distance, i.e. as far as necessary. On full completion of this third insertion distance, the drive element 3 is no longer retained relative to the housing by the retaining element 6. Due to the contact between the proximal end of the holder element 2 and the distal end of the activator element 7, the drive element 3 is also moved in the proximal direction across the third insertion distance relative to the housing. As this happens, the drive knob 8 is moved out of the proximal end of the housing 1 and can now be accessed by the user. During the relative movement of the drive element 3 and with it the activator element 7 relative to the housing 1, the activator element 7 slides along the inwardly projecting edge of the projection 11 and is thus deflected inwardly. The third insertion distance, which corresponds to the stroke of the drive element 3 out of the housing, also corresponds to the distance of forward movement needed to move the drive element forward in the distal direction to dispense the product. The third insertion distance therefore corresponds to a dose setting stroke for the administering device. The insertion distance can therefore be varied depending on the stroke needed to set the dose when designing the administering device.

Figure 4B:
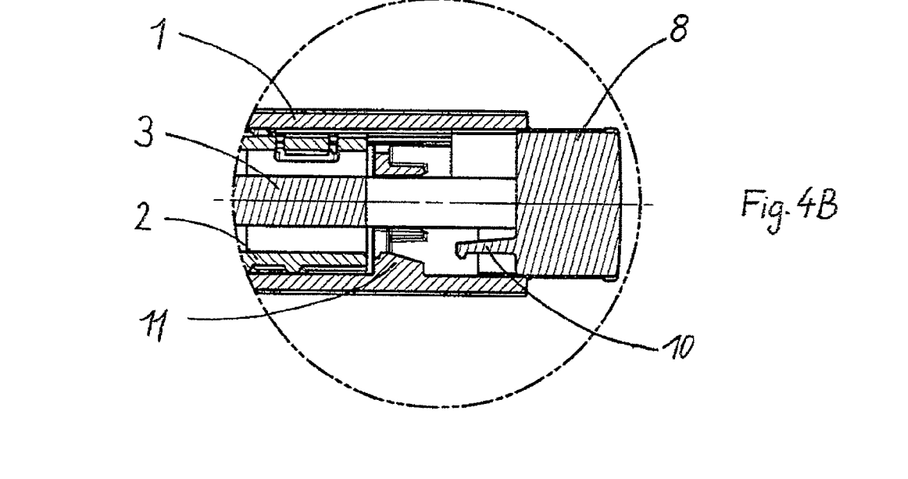
FIG. 4B is a detailed view similar to that of FIG. 1B, in an inserted position.

FIG. 4B is a detailed illustration similar to that shown in FIG. 1B, in which the administering device is shown in an inserted position. As the drive element 3 is moved out of the housing 1, the clamped seating between the lock element 10 and projection 11 is also overcome.

The holder element 2 is now fully screwed into the housing 1, the agent mixed and the product chamber primed. The administering device has been switched to an activated state with the drive knob extracted. It is now ready to administer the desired dose of agent.

Figures 5A, 5B:
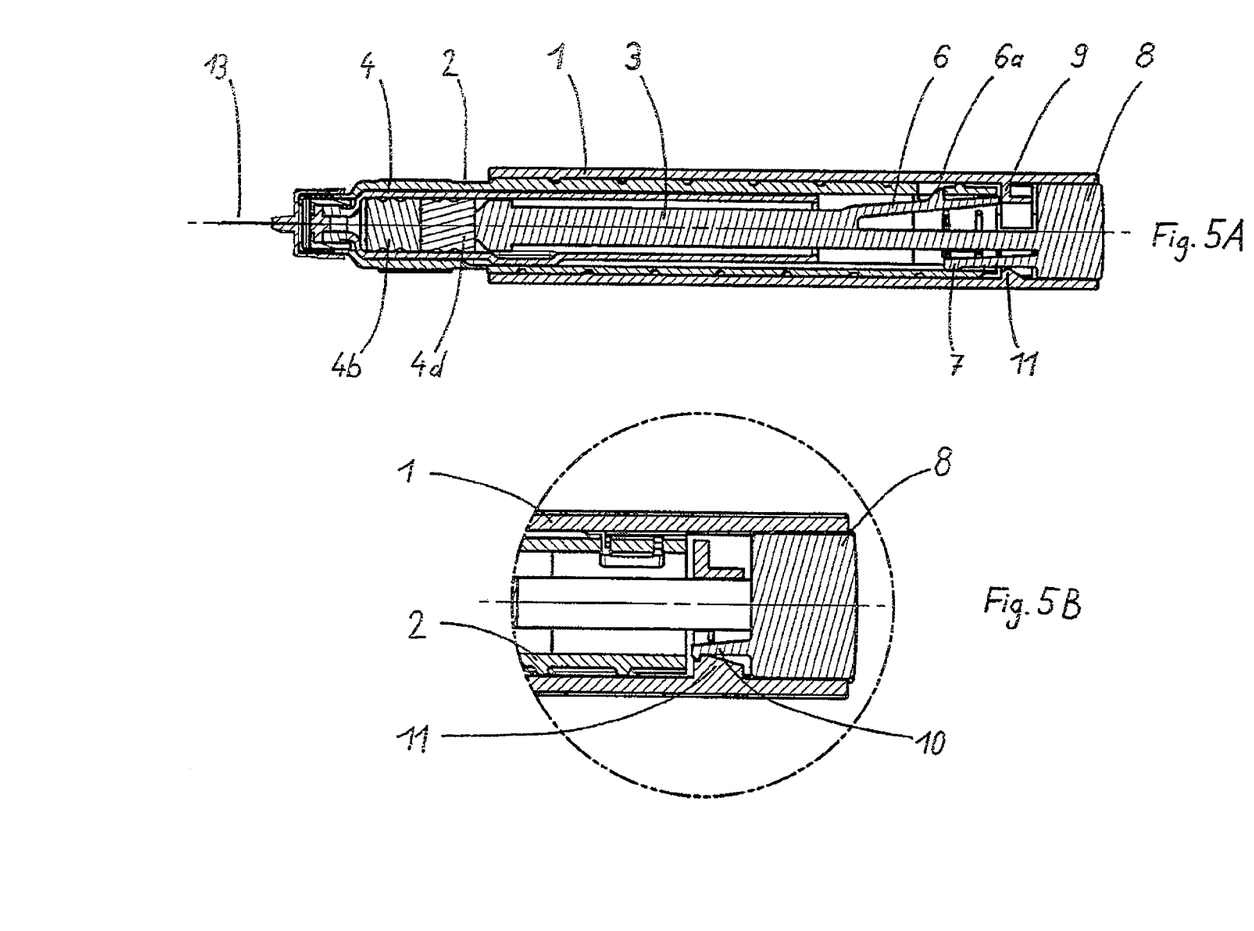
FIG. 5A illustrates the administering device of FIG. 1A in an end position.
FIG. 5B is a detailed view similar to that of FIG. 1B in the end position.

To this end, as illustrated in FIG. 5A, the holder element 2 is pushed in the distal direction into the housing 1, during which the holder element 2 remains stationary with respect to the housing 1. This forward movement is therefore transmitted to the stoppers 4b and 4d so that the liquid product is dispensed from the product chamber 4a. The drive element 3 is pushed into the housing until the drive knob 8 has moved into contact with the housing projection 9. At the same time, the activator element 7, which has been deflected inward by the projection 11, slides on the internal face of the holder element 2 into the holder element 2. The retaining element 6 also slides along the internal surface of the holder element 2. As this happens, the shoulder 6a is guided along the circumferential surface of the holder element 2. As soon as the drive knob 8 makes contact with the housing projection 9, the proximal end of the retaining element 6 is also moved past the housing projection 9. A cut-out is provided in the internal circumferential surface of the holder element 2 on a level with the shoulder 6a, into which the shoulder 6a can flex. Due to the biasing action of the retaining element 6, the latter snaps into the cut-out and back into the retaining position in which the distal end of the retaining element 6 sits in contact with the housing projection 9. The drive knob 8 is retracted inside the housing 1 again.

The administering device is now in an end position. The retaining element 6 is therefore back in a retaining position so that the drive element 3 is secured relative to the housing 1. The administering device is therefore blocked or locked, preventing its operation. FIG. 5B illustrates a detail from FIG. 1B, with the administering device in an end position. As illustrated, the lock element 10 moves back into a clamped seating with the projection 11 of the housing 1. As a result, in addition to the retaining action between the retaining element 6 and housing projection 9, the drive element 3 is also secured to prevent any other movements or wobbling. The administering device can now be disposed of in this secured state.

It should be appreciated that, for the purposes of the present invention, it is sufficient if the drive element 3 is secured by the retaining element 6 to prevent any proximal movement relative to the housing. The lock element 10 makes handling more comfortable and serves as an additional guide for the drive element 3.

Figures 6A, 6B:
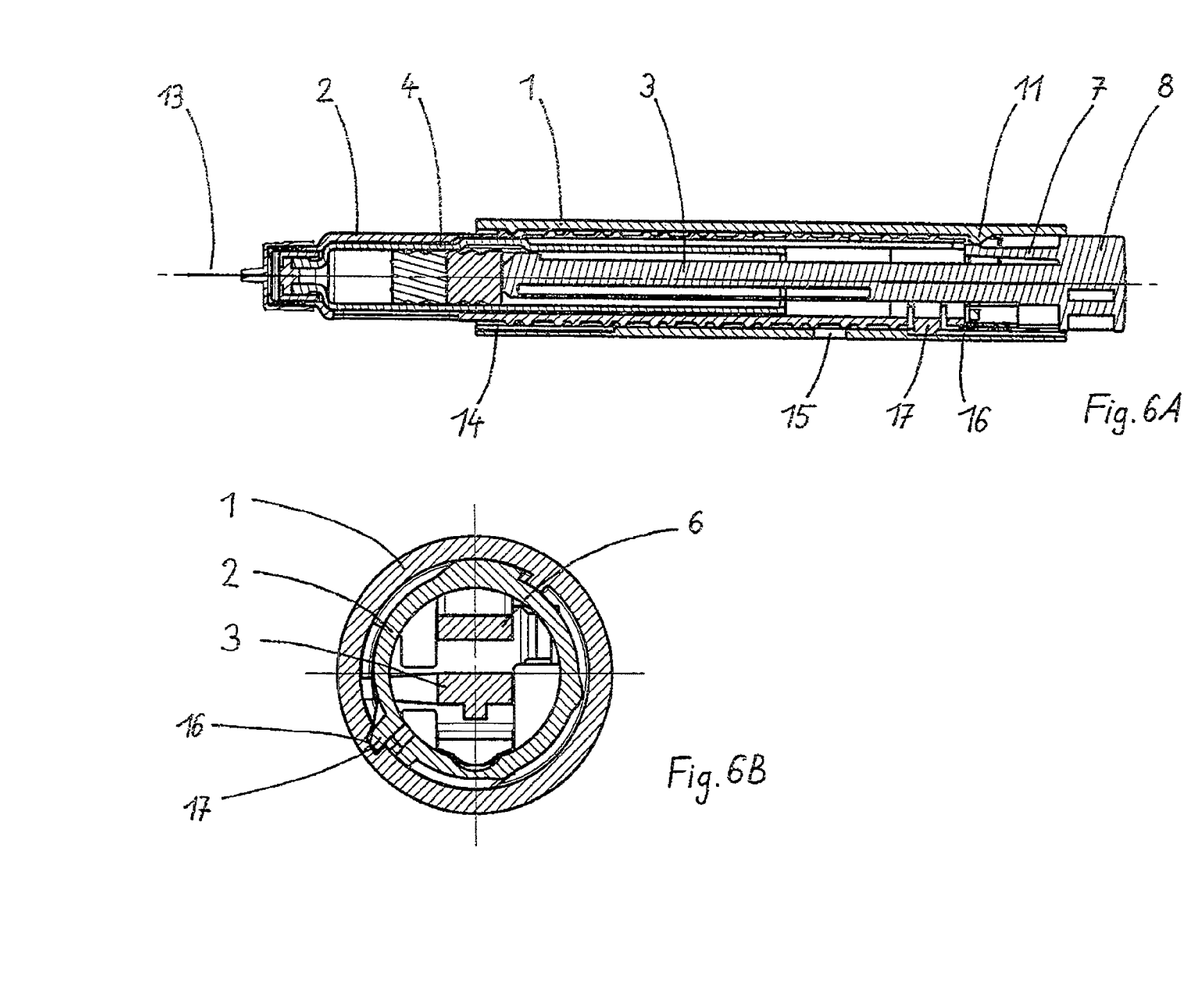
FIG. 6A is a longitudinal section through the administering device based on the first embodiment with a catch mechanism.
FIG. 6B shows the administering device illustrated in FIG. 6A in a priming position.

FIG. 6A shows a section through an administering device, illustrating the catch mechanism or indicator mechanism for latching and providing an indication of the individual steps involved in preparing the administering device. FIG. 6A illustrates the administering device already in a mixing position. The indicator or catch mechanisms comprise a first catch groove 14, a second catch groove 15 which may also be termed a catch orifice, and a third catch groove 16. A catch arm 17 oriented in the circumferential direction is provided on the holder element 2, which is biased radially outwardly so that it slides along the internal circumferential surface of the housing when the holder element 2 is screwed into the housing 1. As the holder element 2 is inserted in the housing 1, the holder element 2 is screwed into the housing 1 until the catch arm 17 latches in the first catch groove 14. In this latched state, the administering device is in the initial position. In some embodiments, the latching action generates an acoustic signal, indicating that the initial position has been reached. The catch arm 17 is designed so that its biasing action prevents the holder element 2 from being screwed back out or pulled back out of the housing due to the contact with the first catch groove 14. From the initial position, the holder element 2 can only be screwed further into the housing 1 in the proximal direction. In principle, it is possible for the first catch groove to be disposed across the length of the housing so that a latching action takes place after every rotation of the holder element, thereby also generating an acoustic signal. From the initial position, the holder element is moved farther in until it latches in the second catch orifice 15 via the catch arm 17, thereby indicating the end of mixing in the two-chamber reservoir. If the second catch groove is provided in the form of an orifice, it is theoretically possible for the catch arm 17 to be pushed from outside toward the interior out of the catch orifice so that the holder element can also be screwed back out of the housing 1. This option might be of practical advantage in some embodiments if the intention is that the operation of administering from the administering device should not take place immediately after mixing. In some embodiments, however, the second catch groove is not provided in the form of an orifice and this second latching action constitutes a lock to prevent the holder element from being screwed back out of the housing. From this mixing position, the holder element can be screwed farther into the housing in the proximal direction until the catch arm 17 is latched in the third catch groove 16, thereby indicating the priming position. The latching action between the catch arm 17 and third catch groove 16 also acts as an anti-rotation lock so that the holder element is locked in this position to prevent any further movement relative to the housing because the holder sleeve 2 also is in contact with the housing projection 9 in the axial direction.

FIG. 6B illustrates a cross-section through the administering device, in which the catch arm 17 holds the holder element 2 in a latched position with a catch groove in the housing 1. As illustrated in FIG. 6B, the holder element 2 can not be turned anti-clockwise due to the latched arrangement, whereas it is possible to turn the holder element 2 in the clockwise direction inside the housing 1 because the catch arm 17 is able to snap flexibly inward and slide along the oblique surface of the groove and out of the groove.

Figure 7:
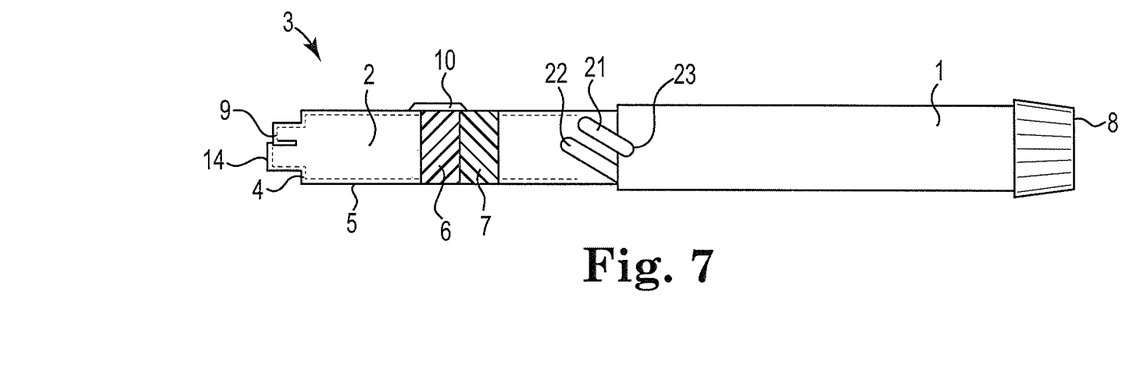
FIG. 7 is a schematic diagram illustrating another embodiment of an administering device in accordance with the present invention with an embodiment of a visual display in accordance with the present invention.

FIG. 7 illustrates another embodiment of an administering device in accordance with the present invention. This embodiment has a housing 1, a drive knob 8 for implement the administering operation and a holder element 2 with a two-chamber carpule 4. The two-chamber carpule has two stoppers 4b and 4d. The agent is contained in the first chamber 4a of the carpule shown on the left-hand side of the diagram between the wall of the carpule, a front opening in the carpule and the stopper 4d. In FIG. 7, the two-chamber carpule is illustrated in a mixed position already and there is no longer a chamber containing dissolving liquid between the stopper 4b and the stopper 4d because the dissolving liquid has already passed from the second chamber through a bypass 12 in the carpule wall into the first chamber 4a.

Disposed on the holder element 2 is a first display 21 in the form of a flag, which indicates the position of the carpule 4 relative to the housing 1 at the end of mixing. In addition to the flag 11, a second display 22 is provided in the form of another flag, which indicates the position of the carpule relative to the housing after priming.

Figure 8:
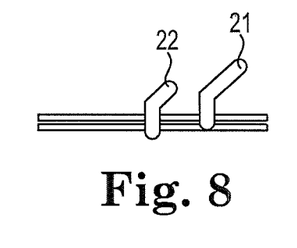
FIG. 8 is a schematic diagram of the display elements illustrated in FIG. 7.

FIG. 8 provides a schematic illustration of the two flags 21 and 32. The flags may be provided in the form of an adhesive label on the carpule sleeve or on the carpule itself. The flags are of different colours and show different print in accordance with their function. They are disposed along the longitudinal axis of the administering device and are offset from one another in the circumferential direction of the administering device. It should be appreciated that the flags are disclosed as one exemplary embodiment of suitable graphics or other indicia that may be used for the display(s).

In FIG. 7, a cut-out 23 is provided at the left-hand edge of the housing 1 of the administering device, which serves as a pointer for selecting or identifying the first and second display or flags 21 and 22. The pointer in the form of the cut-out 23 is therefore integral with the housing and the displays 21 and 22 in the form of the flags can be moved on the carpule sleeve relative to the housing. The device illustrated in FIG. 7 has already undergone the mixing process but has not yet been primed or vented.

When the holder element 2 is now screwed into the housing 1 to mix the two-chamber carpule 4, the flags 21 and 22 change position both axially and in the circumferential direction relative to the housing due to the rotating movement. When mixing of the two-chamber carpule has ended, the flag 21 moves inside the cut-out 23. A user can therefore easily tell that the mixing operation has been fully completed. When the holder element 2 is screwed further into the housing 1, the stoppers 4b and 4d are pushed further inside the two-chamber carpule 4 toward the opening and a quantity of air left in the first chamber 4a of the carpule is able to escape through the opening and through the fitted needle unit 13. Once the rotating movement needed for priming has been completed, the second display with the flag 22 moves into the cut-out 23. The user can therefore see that the priming operation has also been fully completed. The administering device with the two-chamber carpule is now ready for administering the mixed agent.

For more details of a two-chamber carpule and mixing mechanism, reference may be made to the publications mentioned herein above, which are incorporated herein by reference as regards the technical teaching describing two-chamber carpules and mixing mechanisms.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An administering device for administering an agent from a multi-chamber carpule with at least a first chamber containing a solid agent and a second chamber containing a dissolving liquid for the agent, the administering device having a proximal end and a distal end and comprising a housing and a mixing mechanism for mixing the agent and dissolving liquid, wherein the mixing mechanism comprises a holder element for accommodating the carpule, the holder element rotatably moveable relative to the housing for being inserted into the housing and for mixing the agent and dissolving liquid, the multi-chamber carpule fixed relative to the holder element during mixing, the administering device further comprising a display system comprising at least a first visual display for indicating a position of the multi-chamber carpule relative to the housing when a mixing operation has ended, at least a second visual display for indicating a position of the carpule relative to the housing when a priming operation has ended, and a catch mechanism for forming a releaseable catch position between the holder element and the housing which permits rotating the holder element to move the holder element in the proximal direction relative to the housing and non-releasable catch positions between the holder element and the housing which prevent the holder element from moving in the proximal direction relative to the housing, wherein the first visual display and second visual display are at least one of disposed axially offset along a longitudinal axis of the administering device and offset in the circumferential direction on a circumference of the administering device.

2. The administering device as claimed in claim 1, wherein the display system comprises a third visual display for indicating an initial position of the carpule relative to the housing prior to a mixing operation.

3. The administering device as claimed in claim 1, wherein the display system comprises said first visual display and second visual display and at least one of an acoustic signal and a combination of a visual marking and acoustic signal.

4. The administering device as claimed in claim 1, further comprising one of a pointer or cut-out associated with one of the holder element and housing, by which one of the first visual display and second visual display can be displayed, the other of the holder element and housing comprising the display system.

5. The administering device as claimed in claim 1, wherein an insertion movement of the holder element is a rotating movement and in the releasable catch position the catch mechanism acts as a releasable anti-rotation lock to allow the rotating movement of the insertion movement or a rotating movement opposite to the rotating movement of the insertion movement.

6. An administering device for administering an agent from a multi-chamber carpule with at least a first chamber containing a solid agent and a second chamber containing a dissolving liquid for the agent, the administering device having a proximal end and a distal end and comprising:
a housing;
a mixing mechanism for mixing the agent and dissolving liquid, wherein the mixing mechanism comprises a holder element for accommodating the carpule, the holder element rotatably moveable relative to the housing for being inserted into the housing and for mixing the agent and dissolving liquid, the multi-chamber carpule fixed relative to the holder element during mixing;
a display system comprising at least a first visual display for indicating a position of the multi-chamber carpule relative to the housing when a mixing operation has ended, at least a second visual display for indicating a position of the carpule relative to the housing when a priming operation has ended, wherein the first visual display and second visual display are at least one of disposed axially offset along a longitudinal axis of the administering device and offset in the circumferential direction on a circumference of the administering device; and
a catch mechanism for forming a releaseable catch position between the holder element and the housing which permits rotating the holder element to move the holder element in the proximal direction relative to the housing and non-releasable catch positions between the holder element and the housing which prevent the holder element from moving in the proximal direction relative to the housing, wherein the catch mechanism is for latching and providing an indication of individual steps involved in preparing the administering device for use, and comprises a first catch groove, a second catch groove or orifice, a third catch groove, and a catch arm on the holder element oriented in the circumferential direction of the holder element and biased radially outwardly so the arm slides along an internal circumferential surface of the housing when the holder element is rotated into the housing, wherein the holder element is rotated into the housing until the catch arm latches in the first catch groove generating an acoustic signal indicating an initial position has been reached, the initial position constituting a lock preventing the holder element from moving in the proximal direction relative to the housing and from which initial position the holder element is rotated farther in until the arm latches in the second catch groove or orifice reaching a mixing position, generating an acoustic signal indicating the end of mixing of the agent and dissolving liquid and constituting a releasable lock wherein by the holder element can be moved in the proximal direction relative to the housing or can be rotated farther into the housing until the catch arm is latched in the third catch groove generating an acoustic signal indicating an priming position has been reached reaching and constituting an anti-rotation lock so that the holder element is locked in the priming position to prevent any further movement relative to the housing.

7. The administering device according to claim 6, wherein in the priming position a portion of the holder element is in contact with a portion of the housing.

8. The administering device according to claim 6, wherein in the mixing position the catch arm can be pushed from outside the device toward the interior of the device out of the second catch groove or orifice so the holder element can be moved in the proximal direction relative to the housing.

9. A method of preparing an administering device to administer an active substance from a multi-chamber container comprising a first chamber holding a solid active substance and a second chamber holding a dissolving liquid for the active substance, wherein the administering device comprises a mixing device for mixing the active substance with the dissolving liquid and a housing accommodating the mixing device, the multi-chamber container being fixed relative to the mixing device and the mixing device and multi-chamber container together being rotatably moveable relative to the housing during mixing, and the administering device further comprising a display system comprising a first visual indicator for indicating a position of the multi-chamber container relative to the housing upon completion of a mixing operation, and a second visual indicator for indicating a position of the multi-chamber container relative to the housing upon completion of a venting operation, wherein the displays are at least one of disposed axially offset along a longitudinal axis of the administering device and offset in the circumferential direction on a circumference of the administering device, the method comprising the steps of:
performing a mixing operation;
indicating the end of the mixing operation using the first indicator;
performing a venting operation; and
indicating the end of the venting operation using the second indicator.

10. The method according to claim 9, wherein at least one of said indicating steps further comprises audible indicating.

* * * * *